(12) United States Patent
Senetar et al.

(10) Patent No.: US 10,538,466 B2
(45) Date of Patent: Jan. 21, 2020

(54) USE OF C4 ABSORBER OVERHEAD FOR STRIPPING ALDEHYDES

(71) Applicants: UOP LLC, Des Plaines, IL (US); TPC Group, LLC, Houston, TX (US)

(72) Inventors: John J. Senetar, Naperville, IL (US); Jeannie M. Blommel, Oregon, WI (US); Charles P. Luebke, Mount Prospect, IL (US); Dana K. Sullivan, Mount Prospect, IL (US); Joseph G. Duff, League City, TX (US); Jillian M. Horn, Decatur, GA (US); Clifford A. Maat, Pearland, TX (US); Michael O. Nutt, Pearland, TX (US)

(73) Assignees: UOP LLC, Des Plaines, IL (US); TPC Group, LLC, Dallas, TX (US)

(*) Notice: Subject to any disclaimer, the term of this patent is extended or adjusted under 35 U.S.C. 154(b) by 5 days.

(21) Appl. No.: 15/968,909

(22) Filed: May 2, 2018

(65) Prior Publication Data

US 2018/0258015 A1 Sep. 13, 2018

Related U.S. Application Data

(63) Continuation of application No. PCT/US2016/060641, filed on Nov. 4, 2016.

(60) Provisional application No. 62/252,053, filed on Nov. 6, 2015.

(51) Int. Cl.

| C07C 1/24 | (2006.01) |
|---|---|
| C07C 11/167 | (2006.01) |
| C07C 7/11 | (2006.01) |
| C07C 7/09 | (2006.01) |
| C07C 5/48 | (2006.01) |
| C07C 7/00 | (2006.01) |
| B01D 19/00 | (2006.01) |
| C07C 7/04 | (2006.01) |
| B01L 3/14 | (2006.01) |
| B01J 19/00 | (2006.01) |
| C07C 5/42 | (2006.01) |

(52) U.S. Cl.
CPC .......... *C07C 11/167* (2013.01); *B01D 19/0015* (2013.01); *B01J 19/0053* (2013.01); *B01L 3/14* (2013.01); *C07C 1/24* (2013.01); *C07C 5/42* (2013.01); *C07C 5/48* (2013.01); *C07C 7/005* (2013.01); *C07C 7/04* (2013.01); *C07C 7/09* (2013.01); *C07C 7/11* (2013.01); *B01D 2256/24* (2013.01); *B01D 2257/70* (2013.01)

(58) Field of Classification Search
CPC .................. C07C 5/42; C07C 5/48

USPC ......................................... 585/507
See application file for complete search history.

(56) References Cited

U.S. PATENT DOCUMENTS

| 3,528,910 | A | 9/1970 | Haney et al. |
|---|---|---|---|
| 3,563,912 | A | 2/1971 | Young |
| 3,884,650 | A * | 5/1975 | Woerner ............... C07C 7/11 |
| | | | 95/162 |
| 3,935,244 | A | 1/1976 | Hayes |
| 4,066,538 | A | 1/1978 | Cines et al. |
| 4,177,136 | A | 12/1979 | Herrington et al. |
| 4,595,788 | A | 6/1986 | Yamamoto et al. |
| 4,719,195 | A | 1/1988 | Toulhoat et al. |
| 5,520,722 | A | 5/1996 | Hershkowitz et al. |
| 6,291,391 | B1 | 9/2001 | MacArthur |
| 7,513,990 | B2 | 4/2009 | Guillaume et al. |
| 9,353,054 | B2 | 5/2016 | Humblot et al. |
| 9,504,993 | B2 | 11/2016 | Han et al. |
| 2013/0289313 | A1 | 10/2013 | Franke et al. |
| 2014/0200380 | A1 | 7/2014 | Josch et al. |

FOREIGN PATENT DOCUMENTS

| CN | 102826950 | | 12/2012 | | |
|---|---|---|---|---|---|
| EP | 0969931 | A1 | 1/2000 | | |
| EP | 1299192 | A1 | 4/2003 | | |
| WO | 2001097971 | A1 | 12/2001 | | |
| WO | 2011011200 | A2 | 1/2011 | | |
| WO | 2013148913 | A1 | 10/2013 | | |
| WO | WO-2013148908 | A1 * | 10/2013 | ............... | C07C 5/48 |
| WO | WO-2014138520 | A2 * | 10/2014 | ............... | C07C 5/48 |

OTHER PUBLICATIONS

American Chemistry Council's Olefins Panel Butadiene Product Stewardship Task Group, Butadiene Product Stewardship Guidance Manual, Apr. 2, 2010.
International Search Report for PCT/US2016/060641, dated Feb. 27, 2017.
Written Opinion for PCT/US2016/060641, dated Feb. 27, 2017.
Criterion Catalysts Technical Bulletin: Criterion* Hydrotreating catalyst in-Situ Presulphiding Guidelines.

* cited by examiner

*Primary Examiner* — Sharon Pregler
(74) *Attorney, Agent, or Firm* — Greer, Burns & Crain Ltd.

(57) ABSTRACT

A process is presented for the production of butadienes. The process includes the separation of oxygenates from the product stream from an oxidative dehydrogenation reactor. The process includes quenching the product stream and solvent and oxygenates from the product stream. The oxygenates are stripped from the solvent with an inert gas to reduce the energy consumption of the process, and the solvent is recycled and reused in the process.

20 Claims, 1 Drawing Sheet

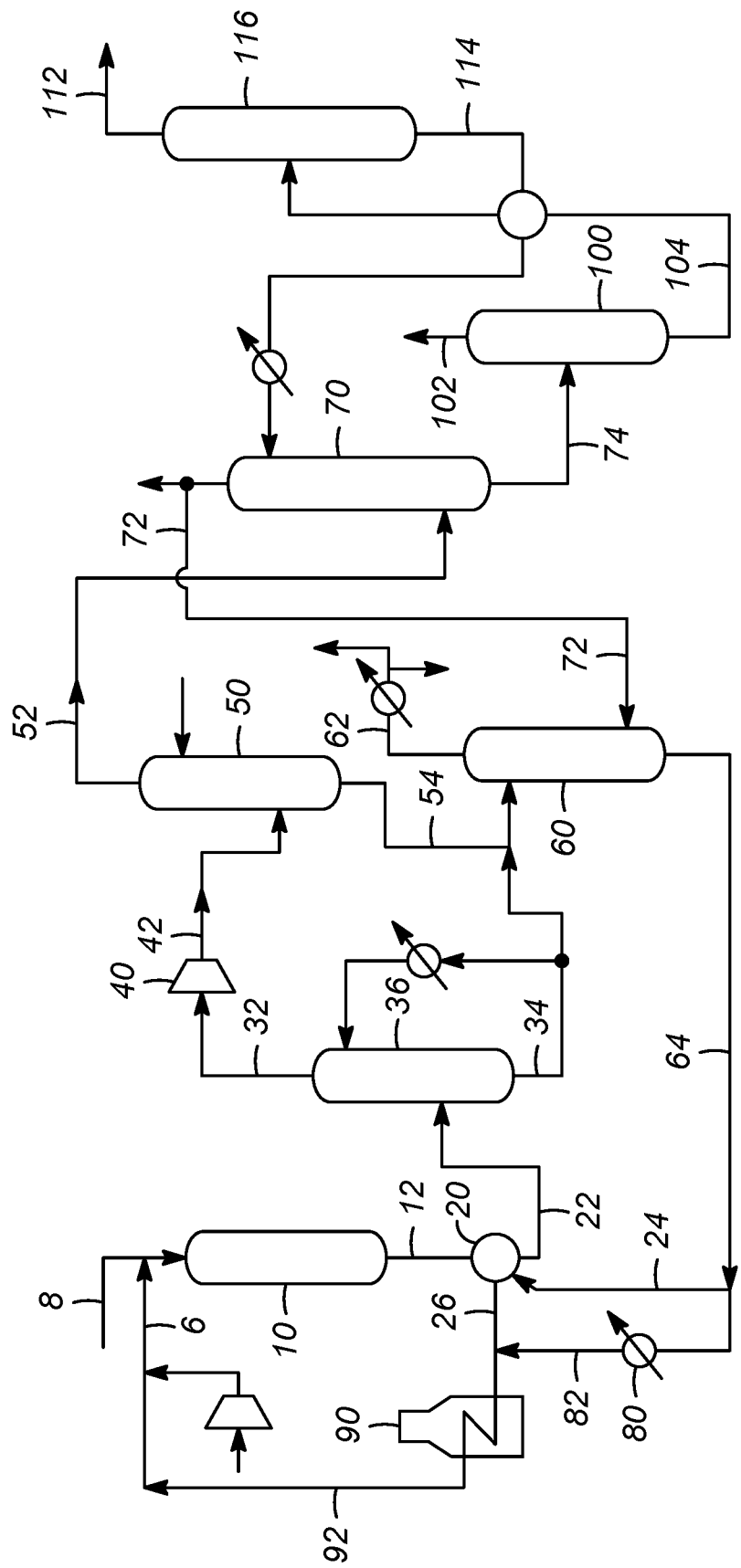

USE OF C4 ABSORBER OVERHEAD FOR STRIPPING ALDEHYDES

STATEMENT OF PRIORITY

This application is a continuation of co-pending International Application No. PCT/US2016/60641, entitled USE OF C4 ABSORBER OVERHEAD FOR STRIPPING ALDEHYDES, filed Nov. 4, 2016, which claims the benefit of U.S. Provisional Application No. 62/252,053, entitled USE OF C4 ABSORBER OVERHEAD FOR STRIPPING ALDEHYDES ON-PURPOSE BUTADIENE PRODUCTION, filed Nov. 6, 2015, the contents of each of which is hereby incorporated by reference in its entirety.

FIELD OF THE INVENTION

The present invention relates to the production of butadiene. In particular, the invention relates to streamlining the process.

BACKGROUND

Butadiene is an important chemical for the production of commercial polybutadiene rubbers, such as those used in the production of tires. Polybutadiene is a desirable rubber due to its resistance to wear, and its high elastic resilience. The sources of butadiene traditionally are a by-product from naphtha cracking. As demand for ethylene and propylene increase, the demand to convert more naphtha to ethylene and propylene reduces the yields for C4 and heavier hydrocarbons from naphtha cracking. This results in a smaller source of material for the production of butadienes.

As demand increases for butadienes, in spite of the demand increases for ethylene and propylene, other sources of C4 compounds are needed. C4 compounds include butanes butenes and butadienes. New sources include fluidized catalytic cracking sources, methanol to olefins, ethylene dimerization, and dehydrogenation of butanes recovered from natural gas fields or oil fields. With the new sources, new processes are needed to efficiently produce and recover butadienes.

The production of a polymer precursor requires many steps. The process can be improved through reducing energy requirements and providing for better management of the process streams.

SUMMARY

The present invention is an improvement in the process of butadiene production. A first embodiment of the invention is a process for the removal of oxygenates from a butadiene reactor effluent stream comprising passing the butadiene reactor effluent stream to a quench tower; cooling and quenching the butadiene reactor effluent stream to generate an overhead stream comprising C4 hydrocarbons, and a bottoms stream comprising solvent and oxygenates; passing the bottoms stream to an oxygenate stripper; and passing an inert gas to the oxygenate stripper, and generating a stripper overhead stream comprising oxygenates and the inert gas, and a stripper bottoms stream comprising solvent. An embodiment of the invention is one, any or all of prior embodiments in this paragraph up through the first embodiment in this paragraph wherein the solvent is water. An embodiment of the invention is one, any or all of prior embodiments in this paragraph up through the first embodiment in this paragraph further comprising passing the butadiene reactor effluent to a heat exchanger to generate steam, and a cooled butadiene reactor effluent, before passing the butadiene reactor effluent to the quench tower. An embodiment of the invention is one, any or all of prior embodiments in this paragraph up through the first embodiment in this paragraph further comprising passing the overhead stream to a compression unit to generate a compressed C4 stream. An embodiment of the invention is one, any or all of prior embodiments in this paragraph up through the first embodiment in this paragraph further comprising passing the compressed C4 stream to an oxygenate scrubber to generate a scrubbed C4 stream and a scrubber bottoms stream. An embodiment of the invention is one, any or all of prior embodiments in this paragraph up through the first embodiment in this paragraph further comprising passing the scrubber bottoms stream to the oxygenate stripper. An embodiment of the invention is one, any or all of prior embodiments in this paragraph up through the first embodiment in this paragraph further comprising passing the scrubbed C4 stream to a C4 absorber to generate an absorber overhead stream comprising the inert gas, and an absorber bottoms stream comprising C4 compounds and solvent. An embodiment of the invention is one, any or all of prior embodiments in this paragraph up through the first embodiment in this paragraph further comprising passing the C4 stripper bottoms stream to the C4 absorber. An embodiment of the invention is one, any or all of prior embodiments in this paragraph up through the first embodiment in this paragraph further comprising passing the absorber bottoms stream to a degasser to generate a erhead stream and a degasser bottoms stream comprising solvent and C4 compounds. An embodiment of the invention is one, any or all of prior embodiments in this paragraph up through the first embodiment in this paragraph further comprising passing the degasser bottoms stream to a C4 stripper to generate a C4 product stream and a bottoms stream comprising solvent. An embodiment of the invention is one, any or all of prior embodiments in this paragraph up through the first embodiment in this paragraph further comprising passing a butene stream to an oxidative dehydrogenation reactor, to generate the butadiene reactor effluent stream. An embodiment of the invention is one, any or all of prior embodiments in this paragraph up through the first embodiment in this paragraph wherein the oxidative dehydrogenation reactor comprises a two stage reactor system, with the two reactors connected in series and the butene stream passing from the first reactor to the second reactor, and with an oxidizing agent and steam passed to both reactors.

A second embodiment of the invention is a process for the production of butadienes, comprising passing a butene stream to a oxidative dehydrogenation reactor; passing superheated steam and compressed air to the oxidative dehydrogenation reactor, to generate an effluent stream comprising butadienes; passing the effluent stream, and water through a heat exchanger to generate a cooled effluent stream and a steam stream; passing the cooled effluent stream to a quench tower to generate a quenched C4 stream and a quench bottoms stream; passing the quenched C4 stream to a compressor to generate a compressed C4 stream; passing the compressed C4 stream to an aldehyde scrubber to generate a C4 product stream, and a scrubber bottoms stream; passing the scrubber bottoms stream and the quench bottoms stream to an aldehyde stripper; and passing an inert gas stream to the aldehyde stripper to generate a stripper overhead stream and a bottoms water stream. An embodiment of the invention is one, any or all of prior embodiments in this paragraph up through the second embodiment in this paragraph wherein the quench bottoms stream is passed along with the scrubber bottoms stream to the aldehyde stripper. An embodiment of the invention is one, any or all of prior embodiments in this paragraph up through the second embodiment in this paragraph further comprising passing the steam stream to a steam superheater to generate the superheated steam passed to the oxidative dehydrogenation reactor. An embodiment of the invention is one, any or all of prior embodiments in this paragraph up through the second embodiment in this paragraph further comprising passing a portion of the bottoms water stream to the heat exchanger to generate the steam stream. An embodiment of the invention is one, any or all of prior embodiments in this paragraph up through the second embodiment in this paragraph further comprising passing the C4 process stream to a C4 absorber to generate a C4 absorber bottoms stream and a C4 absorber overhead stream, comprising the inert gas. An embodiment of the invention is one, any or all of prior embodiments in this paragraph up through the second embodiment in this paragraph further comprising passing the C4 absorber overhead stream to the aldehyde stripper. An embodiment of the invention is one, any or all of prior embodiments in this paragraph up through the second embodiment in this paragraph further comprising passing the C4 absorber bottoms stream to a degasser to generate a degasser overhead stream and a degasser bottoms stream; passing the degasser bottoms stream to a C4 stripper to generate a C4 overhead stream and a solvent bottoms stream; and passing the C4 overhead stream to a C4 splitter. An embodiment of the invention is one, any or all of prior embodiments in this paragraph up through the second embodiment in this paragraph further comprising passing the solvent bottoms stream to the C4 absorber.

Other objects, advantages and applications of the present invention will become apparent to those skilled in the art from the following detailed description and drawings.

BRIEF DESCRIPTION OF THE DRAWING

The FIGURE shows the process of the present invention using inert gases to strip the water in the production of butadienes.

DETAILED DESCRIPTION

One area of increasing the production of butadienes is on-purpose butadiene production (OPBD). On purpose butadiene production can be performed with direct dehydrogenation of a butane/butene stream, a two step process for the conversion of butane to butadiene, or the oxydehydrogenation of normal butenes to butadiene.

With oxydehydrogenation of normal butenes, an effluent process stream, including C4 compounds, is generated. The effluent process stream also includes oxygenates. The oxygenates need to be removed from the effluent stream of an oxydehydrogenation reactor, before sending the C4 compounds to a butadiene recovery unit.

The oxygenates include ketones, aldehydes and other oxygenates. A principal oxygenate generated in the process are aldehydes. The aldehydes and other oxygenate impurities are removed through absorbing the impurities in a solvent. The solvent is subsequently stripped of the impurities and recycled to the absorbing units.

The present invention is a process for the removal of oxygenates from a butadiene reactor effluent stream. The process includes passing the butadiene reactor effluent stream to a quench tower to cool and quench the effluent stream with a solvent stream. The quench tower generates an overhead stream comprising C4 hydrocarbons, and a bottoms stream comprising solvent and oxygenates. The bottoms stream is passed to an oxygenate stripper to separate the bottoms stream into an overhead stream comprising oxygenates and an inert gas, and a bottoms stream comprising the solvent. An inert gas is passed to the oxygenate stripper to provide the stripping medium to remove the oxygenates from the solvent in the bottoms stream. In one embodiment, the solvent is water.

The process can further includes passing the butadiene reactor effluent to a heat exchanger to precool the reactor effluent and to generate steam. The precooled effluent stream is then passed to the quench tower. The quench tower overhead stream is passed to a compression unit to generate a compressed C4 stream. The compressed C4 stream is passed to an oxygenate scrubber. The oxygenate scrubber generates a scrubbed C4 stream and a scrubber bottoms stream. The residual oxygenates that are not removed by the quench tower are primarily aldehydes. The oxygenate scrubber bottoms stream is passed to the oxygenate stripper.

The scrubbed C4 stream is passed to a C4 absorber column, wherein inert gases in the scrubbed C4 stream are removed and passed out of the absorber column overhead. A solvent is passed to the C4 absorber column and generate a bottoms stream comprising the C4 compounds and solvent. The C4 absorber bottoms stream is passed to a degasser column to generate a degasser overhead stream and a bottoms stream comprising C4 compounds and solvent. The degasser bottom stream is passed to a C4 stripper to separate the solvent from the C4 compounds. The C4 stripper generates an overhead comprising a C4 product stream comprising butadienes and a bottoms stream comprising solvent. The solvent from the C4 stripper bottoms is passed to the C4 absorber.

The inert gas, such as nitrogen, used in the oxygenate stripper saves energy and reduces or eliminates the need for steam generation in the stripper. The oxygenate stripper can also be referred to as the aldehyde stripper due to the primary oxygenates comprise aldehydes generated in the oxidative dehydrogenation reactor. The use of an inert gas over the use of steam allows for a lower temperature operation, as the use of steam requires a higher temperature to prevent condensation of the steam in the oxygenate stripper overhead lines.

The process, as shown in the FIGURE, comprises passing a butene stream 8 to an oxidative dehydrogenation reactor 10. Superheated steam and compressed air 6 are also passed to the reactor 10 to generate an effluent stream 12 comprising butadienes. The effluent stream 12 is passed through a heat exchanger 20 to generate a cooled effluent stream 22. A water stream 24 can be passed through the heat exchanger 20 to generate steam 26. The cooled effluent stream 22 is passed to a quench tower 36 where the effluent stream 22 is further cooled and oxygenates are washed out. The quench tower 36 generates a quenched C4 stream 32 and a quench bottoms stream 34.

The quenched overhead C4 stream 32 is compressed in a compression unit 40 to generate a compressed C4 stream 42. The compression unit 40 can comprise multiple compressors, or multistage compressors, with interstage cooling to condense solvent. The compressed C4 stream 42 is passed to an oxygenate scrubber 50 to generate a scrubbed C4 stream 52. The oxygenate scrubber 50 removes oxygenates and the primary oxygenates removed are aldehydes. The oxygenate scrubber 50 generates a scrubber bottoms stream 54 which is passed to an oxygenate stripper 60. The scrubber bottoms stream 54 is combined with the quench bottoms stream 34 and passed to the oxygenate stripper 60. An inert gas stream 72 is passed to the oxygenate stripper 60 to generate an overhead stream 62, comprising waste gases, and a bottoms stream 64 comprising stripped water. The water stream 64 is recycled and passed to a heat exchanger 20 to generate steam 26 for use in the oxidative dehydrogenation reactors 10. A portion of the water stream 64 can be passed through a vaporizer 80 to generate steam 82. The steam is passed through a superheater 90 to generate the superheated steam 92 passed to the reactors 10.

The process further includes passing the scrubbed C4 process stream 52 to a C4 absorber 70. The C4 absorber 70 absorbs the C4 hydrocarbons from the process stream 52 and generates a C4 absorber overhead stream 72 comprising inert gases, and a C4 bottoms stream 74 comprising C4 hydrocarbons and solvent. The C4 overhead stream 72 provides the inert gas for use in the oxygenate stripper 60.

The C4 bottoms stream is passed to a degasser 100 to remove residual light gases in the degasser overhead stream 102. The degasser 100 generates a bottoms stream 104 comprising degassed solvent and C4 hydrocarbons. The degasser bottoms stream 104 is passed to a C4 stripper 116 to separate the C4 compounds from the absorber solvent. The C4 stripper 116 generates an overhead stream 112 comprising the C4 hydrocarbons, and a bottoms stream 114 comprising solvent. The solvent stream 114 is cooled through heat exchange with the stripper feed stream 104, and the cooled solvent stream 114 is passed to the C4 absorber 70. The C4 overhead stream is passed to a C4 splitter (not shown), to separate the butadienes from the other C4 compounds.

The oxidative dehydrogenation reactor 10 can comprises one or more reactors in series with a heat exchanger between reactors to control the inlet temperatures. In one embodiment, the oxidative dehydrogenation reactor 10 comprises two reactors connected in series and the butene stream passing from the first reactor to the second reactor. Steam and an oxidizing agent are passed to each reactor. A preferred oxidizing agent is compressed air.

The process is improved with the use an existing process stream depleted of oxygenates for stripping in the oxygenate stripper. The overhead, comprising an inert gas, from the downstream C4 absorber provides a good stripping gas for the oxygenate stripper. The overhead from C4 absorber is already destined to be sent to the same downstream treatment, such as a thermal oxidizer, and is the same destination as the overhead of the oxygenate stripper.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for the removal of oxygenates from a butadiene reactor effluent stream comprising:
    passing the butadiene reactor effluent stream to a quench tower;
    cooling and quenching the butadiene reactor effluent stream to generate an overhead stream comprising C4 hydrocarbons, and a bottoms stream comprising solvent and oxygenates;
    passing the bottoms stream to an oxygenate stripper; and
    passing an inert gas to the oxygenate stripper, and generating a stripper overhead stream comprising oxygenates and the inert gas, and a stripper bottoms stream comprising solvent, wherein the inert gas is not steam.

2. The process of claim 1 wherein the solvent is water.

3. The process of claim 1 further comprising passing the butadiene reactor effluent stream to a heat exchanger to generate steam, and a cooled butadiene reactor effluent, before passing the butadiene reactor effluent to the quench tower.

4. The process of claim 1 further comprising passing the overhead stream to a compression unit to generate a compressed C4 stream.

5. The process of claim 4 further comprising passing the compressed C4 stream to an oxygenate scrubber to generate a scrubbed C4 stream and a scrubber bottoms stream.

6. The process of claim 5 further comprising passing the scrubber bottoms stream to the oxygenate stripper.

7. The process of claim 5 further comprising passing the scrubbed C4 stream to a C4 absorber to generate an absorber overhead stream comprising the inert gas, and an absorber bottoms stream comprising C4 compounds and solvent, wherein the inert gas in the absorber overhead stream is the inert gas passed to the oxygenate stripper.

8. The process of claim 7 further comprising passing the absorber bottoms stream to a degasser to generate a degasser overhead stream and a degasser bottoms stream comprising solvent and C4 compounds.

9. The process of claim 8 further comprising passing the degasser bottoms stream to a C4 stripper to generate a C4 product stream and a C4 stripper bottoms stream comprising solvent.

10. The process of claim 9 further comprising passing the C4 stripper bottoms stream to the C4 absorber.

11. The process of claim 1 further comprising passing a butene stream to an oxidative dehydrogenation reactor, to generate the butadiene reactor effluent stream.

12. The process of claim 11 wherein the oxidative dehydrogenation reactor comprises a two stage reactor system, with the two reactors connected in series and wherein an effluent from the first reactor is passed as feed to the second reactor, and with an oxidizing agent and steam passed to both reactors.

13. A process for the production of butadienes, comprising:
    passing a butene stream to a oxidative dehydrogenation reactor;
    passing superheated steam and compressed air to the oxidative dehydrogenation reactor, to generate an effluent stream comprising butadienes;
    passing the effluent stream, and water through a heat exchanger to generate a cooled effluent stream and a steam stream;
    passing the cooled effluent stream to a quench tower to generate a quenched C4 stream and a quench bottoms stream;
    passing the quenched C4 stream to a compressor to generate a compressed C4 stream;
    passing the compressed C4 stream to an aldehyde scrubber to generate a C4 product stream, and a scrubber bottoms stream;
    passing the scrubber bottoms stream to an aldehyde stripper; and
    passing an inert gas stream to the aldehyde stripper to generate a stripper overhead stream and a bottoms water stream, wherein the inert gas is not steam.

14. The process of claim 13 wherein the quench bottoms stream is passed along with the scrubber bottoms stream to the aldehyde stripper.

15. The process of claim 13 further comprising passing the steam stream to a steam superheater to generate the superheated steam passed to the oxidative dehydrogenation reactor.

16. The process of claim 14 further comprising passing a portion of the bottoms water stream to the heat exchanger to generate the steam stream.

17. The process of claim 13 further comprising passing the C4 product stream to a C4 absorber to generate a C4 absorber bottoms stream and a C4 absorber overhead stream, comprising the inert gas.

18. The process of claim 17 further comprising passing the C4 absorber overhead stream to the aldehyde stripper.

19. The process of claim 17 further comprising:
- passing the C4 absorber bottoms stream to a degasser to generate a degasser overhead stream and a degasser bottoms stream;
- passing the degasser bottoms stream to a C4 stripper to generate a C4 overhead stream and a solvent bottoms stream; and
- passing the C4 overhead stream to a C4 splitter.

20. The process of claim 19 further comprising passing the solvent bottoms stream to the C4 absorber.

* * * * *